(12) United States Patent
Xu et al.

(10) Patent No.: US 7,053,260 B2
(45) Date of Patent: May 30, 2006

(54) REDUCING TEMPERATURE DIFFERENCES WITHIN THE REGENERATOR OF AN OXYGENATE TO OLEFIN PROCESS

(75) Inventors: Teng Xu, Houston, TX (US); Paul N. Chisholm, Houston, TX (US); Stephen Neil Vaughn, Kingwood, TX (US); Shun Chong Fung, Bridgewater, NJ (US); Keith Holroyd Kuechler, Friendswood, TX (US); James R. Lattner, Seabrook, TX (US); Kenneth Ray Clem, Humble, TX (US); Patrick J. Maher, Kingwood, TX (US); Dean C. Draemel, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 678 days.

(21) Appl. No.: 10/170,939

(22) Filed: Jun. 13, 2002

(65) Prior Publication Data

US 2003/0163010 A1    Aug. 28, 2003

Related U.S. Application Data

(60) Provisional application No. 60/345,402, filed on Jan. 7, 2002.

(51) Int. Cl.
   *C07C 1/20* (2006.01)
(52) U.S. Cl. ............... 585/638; 585/639; 585/640; 502/38; 502/39; 502/41; 502/42
(58) Field of Classification Search ........ 585/638, 585/639, 640; 502/38, 39, 41, 42
   See application file for complete search history.

(56) References Cited

U.S. PATENT DOCUMENTS

| 4,072,600 A | 2/1978 | Schwartz ............ 208/120 |
| 4,151,121 A | 4/1979 | Gladrow ............. 252/455 |
| 4,350,614 A | 9/1982 | Schwartz ............ 252/455 |
| 4,861,938 A | 8/1989 | Lewis et al. ......... 585/640 |
| 4,973,792 A | 11/1990 | Lewis et al. ........ 585/638 |
| 6,023,005 A | 2/2000 | Lattner et al. ....... 585/639 |
| 6,166,282 A | 12/2000 | Miller ............... 585/638 |

FOREIGN PATENT DOCUMENTS

| EP | 0 040 914 | 2/1981 |
| EP | 1 142 639 | 10/2001 |

*Primary Examiner*—Elizabeth D. Wood

(57) ABSTRACT

The present invention provides a process for making an olefin product from an oxygenate feedstock which comprises:

a) contacting the feedstock in a reaction zone with a catalyst comprising i) a molecular sieve having defined pore openings and ii) a CO oxidation metal, under conditions effective to convert the feedstock into an olefin product stream comprising $C_2$–$C_3$ olefins and to form carbonaceous deposits on the catalyst so as to provide a carbon-containing catalyst;

b) contacting at least a portion of the carbon-containing catalyst with a regeneration medium comprising oxygen in a regeneration zone comprising a fluid bed regenerator having a dense fluid phase and a dilute fluid phase under conditions effective to obtain a regenerated catalyst portion, wherein the difference between the temperature of the dilute phase and the temperature of the dense phase is no greater than 100° C.;

c) introducing said regenerated catalyst portion into said reaction zone; and d) repeating steps a)–c).

36 Claims, 3 Drawing Sheets

REDUCING TEMPERATURE DIFFERENCES WITHIN THE REGENERATOR OF AN OXYGENATE TO OLEFIN PROCESS

This application claims benefit to provisional application No. 60/345,402, filed Jan. 7, 2002.

FIELD OF THE INVENTION

The present invention relates to a method for reducing temperature differences within the regenerator of an oxygenate to olefin process.

BACKGROUND OF THE INVENTION

Light olefins, defined herein as ethylene, propylene, butylene and mixtures thereof, serve as feeds for the production of numerous important chemicals and polymers. Typically, light olefins are produced by cracking petroleum feeds. Because of the limited supply of competitive petroleum feeds, the opportunities to produce low cost light olefins from petroleum feeds are limited. Efforts to develop light olefin production technologies based on alternative feeds have increased.

An important type of alternate feed for the production of light olefins is oxygenate, such as, for example, alcohols, particularly methanol and ethanol, dimethyl ether, methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

The conversion of oxygenates to olefins generates and deposits carbonaceous material (coke) on the molecular sieve catalysts used to catalyze the conversion process. Over accumulation of these carbonaceous deposits will interfere with the catalyst's ability to promote the reaction. In order to avoid unwanted build-up of coke on the molecular sieve catalyst, the oxygenate to olefin process incorporates a second step comprising catalyst regeneration. During regeneration, the coke is removed from the catalyst by combustion with oxygen, which restores the catalytic activity of the catalyst. The regenerated catalyst then may be reused to catalyze the conversion of oxygenates to olefins.

Typically, oxygenate to olefin conversion and regeneration are conducted in two separate vessels. The coked catalyst is continuously withdrawn from the reaction vessel used for conversion to a regeneration vessel and regenerated catalyst is continuously withdrawn from the regeneration vessel and returned to the reaction vessel for conversion.

U.S. Pat. Nos. 6,023,005 and 6,166,282, both of which are incorporated herein by reference, disclose methods of producing ethylene and propylene by catalytic conversion of oxygenate in a fluidized bed reaction process which utilizes catalyst regeneration.

European Patent Application EP 1142639A1 discloses a process for adding an active source of a hydrogenation component dissolved in a non-aqueous solvent to a non-zeolitic molecular sieve catalytic particulate with little or no reduction in micropore volume to provide improved catalytic performance in hydrocracking, catalytic dewaxing, and isomerization of waxy feedstocks to provide improved lubricating oils. The hydrogenation component can be added to the catalyst in the form of a bis (beta-diketonato)metal (II) complex.

U.S. Pat. No. 4,350,614 to Schwartz teaches the introduction of a platinum group metal modified catalyst in a fluidized catalytic cracking (FCC) process in combination with increasing the oxygen input to the regeneration zone to burn carbon monoxide in the dense phase rather than in the dilute phase whereby reducing the temperature differential between the two phases, markedly reducing the temperature of the dilute phase while only moderately increasing the temperature of the dense phase.

U.S. Pat. No. 4,072,600 to Schwartz and U.S. Pat. No. 4,151,121 to Gladrow et al. provide additional disclosures pertaining to the use of platinum group metal in CO oxidation in FCC units. The catalyst containing platinum group metal used for carbon monoxide burning in FCC can be used in the presence of water and is highly active, such that an alumina support can be used.

In the regenerator of a methanol to olefin (MTO) process, in the absence of a CO combustion promoter metal, the oxidation of carbonaceous deposits to CO is fast relative to the conversion of CO to $CO_2$. As a result of its slower rate, the conversion of CO to $CO_2$ is not always complete within the lower dense phase of the fluid bed regenerator. When this reaction occurs in the upper dilute zone, the result is a temperature rise that can easily exceed 100° C. This phenomenon is frequently referred to as "afterburning." Afterburning in the upper dilute phase of a regenerator can lead to excessive temperatures, causing damage or potential failure of the regenerator vessels or other components contained within the vessels.

Many metals are known to promote the oxidation of CO to $CO_2$. An example is the use of Pt or Pd in the catalytic converter of an automobile. However, these same metals are known to catalyze reactions with light olefins and hydrogen, such as hydrogenation or hydrocracking reactions. Such reactions are undesirable in an oxygenates to olefins process, as they would cause a reduction in the yield of these light olefins.

Accordingly, it would be useful to provide a process for making olefins from oxygenate which avoids or reduces afterburning in the regenerator by employing a CO oxidation metal to completely convert the carbonaceous deposits to $CO_2$ within the dense phase of the regenerator, without significantly reducing selectivity to primary olefins in the oxygenate to olefins reactor.

SUMMARY OF THE INVENTION

The present invention solves the current needs in the art by providing a method for converting a feed including an oxygenate to a product including a light olefin. The method of the present invention is conducted in a reactor apparatus. As used herein, the term "reactor apparatus" refers to an apparatus which includes at least a place in which an oxygenate to olefin conversion reaction takes place. As further used herein, the term "reaction zone" refers to the portion of a reactor apparatus in which the oxygenate to olefin conversion reaction takes place and is used synonymously with the term "reactor." Desirably, the reactor apparatus includes a reaction zone, an inlet zone and a disengaging zone. The "inlet zone" is the portion of the reactor apparatus into which feed and catalyst are introduced. The "reaction zone" is the portion of the reactor apparatus in which the feed is contacted with the catalyst under conditions effective to convert the oxygenate portion of the feed into a light olefin product. The "disengaging zone" is the portion of the reactor apparatus in which the catalyst and any additional solids in the reactor are separated from the products. Typically, the reaction zone is positioned between the inlet zone and the disengaging zone.

The present invention relates to a process for making an olefin product from an oxygenate feedstock comprising:

a) contacting the feedstock in a reaction zone with a catalyst comprising i) a molecular sieve having defined pore openings and ii) a CO oxidation metal, under conditions effective to convert the feedstock into an olefin product stream comprising $C_2$–$C_3$ olefins and to form carbonaceous deposits on the catalyst so as to provide a carbon-containing catalyst;

b) contacting at least a portion of the carbon-containing catalyst with a regeneration medium comprising oxygen in a regeneration zone comprising a fluid bed regenerator having a dense fluid phase and a dilute fluid phase under conditions effective to obtain a regenerated catalyst portion, wherein the difference between the temperature of the dilute phase and the temperature of the dense phase is no greater than 100° C.;

c) introducing said regenerated catalyst portion into said reaction zone; and d) repeating steps a)–c).

In one embodiment, said difference in temperature is no greater than 50° C., no greater than 20° C., or even no greater than 10° C.

In another embodiment, the regenerated catalyst portion has less than 5.0 wt. % carbonaceous deposits, less than 3 wt. % carbonaceous deposits, or even less than 1 wt. % carbonaceous deposits.

In yet another embodiment, the carbon-containing catalyst has no less than 5 wt. % carbonaceous deposits, no less than 3 wt. % carbonaceous deposits, or even no less than 1 wt. % carbonaceous deposits.

In still another embodiment, the CO oxidation metal comprises an element selected from the group consisting of Group VB, Group VIB, Group VIIB, and Group VIII metals.

In another embodiment, the Group VB metal is V (vanadium), said Group VIB metal is selected from the group consisting of Cr, Mo and W, said Group VIIB metal is Mn, and said Group VIII metal is selected from the group consisting of Ni, Ru, Rh, Pd, Os, Ir, and Pt.

In yet another embodiment, the CO oxidation metal comprises Pt.

In another embodiment, the CO oxidation metal is added in a form having an external dimension greater than the diameter of the pore openings of the molecular sieve.

In still another embodiment, the CO oxidation metal is added in the form of platinum acetylacetonate.

In still yet another embodiment, the molecular sieve catalyst has a pore diameter of less than 5.0 Angstroms, e.g, the molecular sieve catalyst comprises at least one molecular sieve framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, and THO. Other suitable molecular sieves include those selected from the group consisting of ZSM-5, ZSM-4, erionite and chabazite, SAPO-34, SAPO-17, SAPO-18, MeAPSO and substituted groups thereof.

In one embodiment, the molecular sieve catalyst has a pore diameter of 5–10 Angstroms, e.g., the molecular sieve catalyst comprises at least one molecular sieve framework-type selected from the group consisting of MFI, MEL, MTW, EUO, MTT, HEU, FER, AFO, AEL, TON, and substituted groups thereof.

In another embodiment of the process of the present invention, the selectivity to ethylene and propylene differs by no more than ±5% to that of a comparable process carried out in the absence of said CO oxidation metal.

In still another embodiment of the process of the present invention, there is no reduction in % selectivity to ethylene and propylene compared to the same process except for being carried out in the absence of said CO oxidation metal.

In yet another embodiment, the CO oxidation metal is present in an amount no greater than 5% based on total catalyst weight, e.g., an amount no greater than 1% based on total catalyst weight, say, in an amount no greater than 5000 ppm based on total catalyst weight, an amount no greater than 500 ppm based on total catalyst weight, or even an amount no greater than 100 ppm based on total catalyst weight.

In still yet another embodiment, the CO oxidation metal is platinum and is present in an amount ranging from 0.1 to 10000 ppm based on total catalyst weight, e.g., the CO oxidation metal is platinum and is present in an amount ranging from 1 to 5000 ppm based on total catalyst weight.

In yet another embodiment, the CO oxidation metal is vanadium and is present in an amount ranging from 5000 to 100000 ppm catalyst weight, e.g., 10000 to 50000 ppm based on total catalyst weight.

In one embodiment of the process of the present invention, the CO oxidation metal is added to the process separately from said catalyst.

In another embodiment, the CO oxidation metal is added to the process through the regeneration zone.

In still another embodiment, the CO oxidation metal is added to the process through the reaction zone.

In yet another embodiment, the CO oxidation metal is added to the catalyst by ion exchange.

In another embodiment, a temperature of 500° to 750° C. is maintained within the dense fluid phase of the regenerator.

In still another embodiment, the dispersion level of the CO oxidation metal is "low to moderate", defined for Pt as H:Pt ratio of 0.1 to 0.7

DETAILED DESCRIPTION OF THE INVENTION

Molecular Sieves and Catalysts thereof

Figure 1:
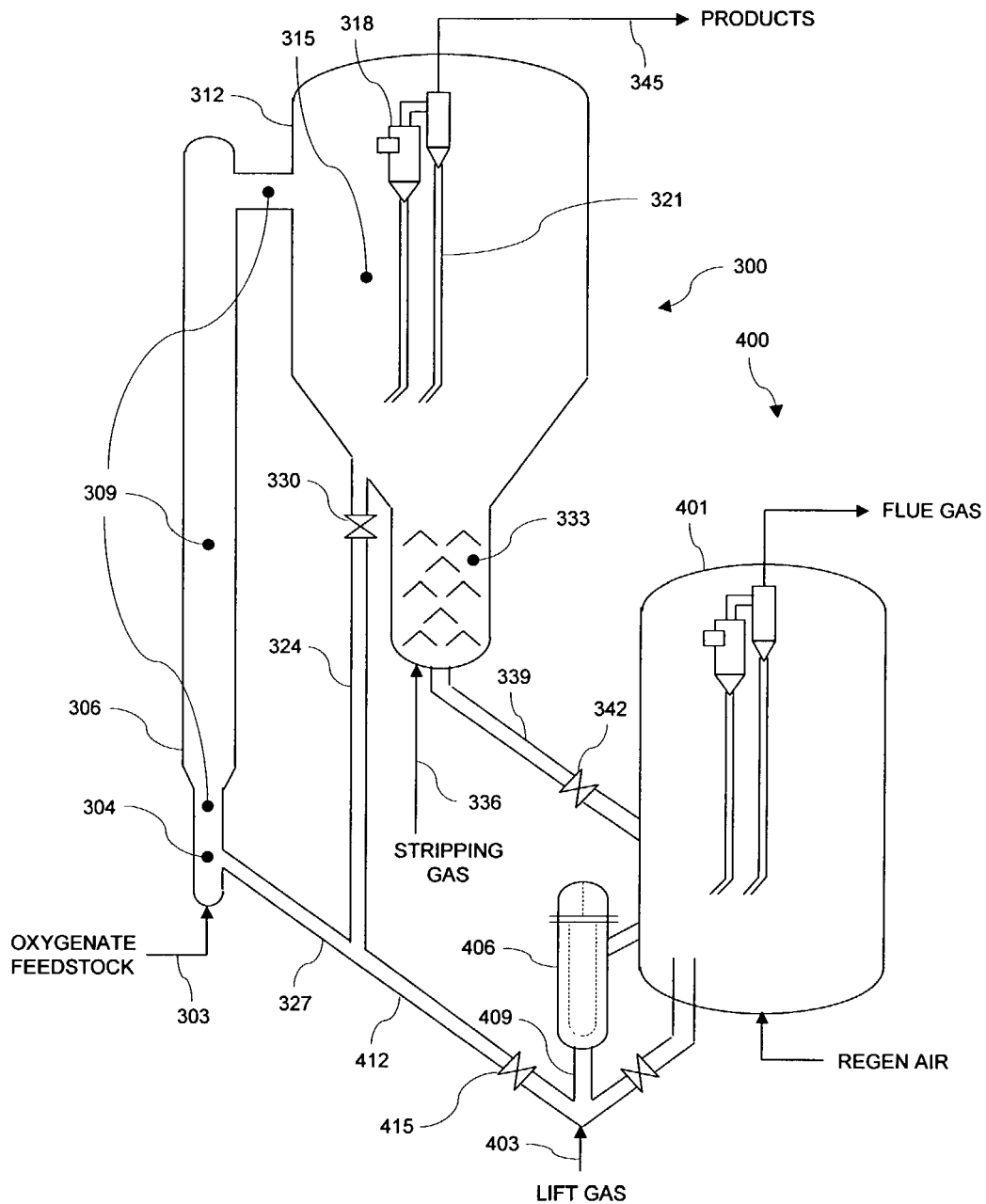
FIG. 1 depicts a reactor apparatus comprising a high velocity fluid bed with catalyst recirculation, and a regenerator for use in the oxygenate to olefin process of the present invention.

Molecular sieves have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the Atlas of Zeolite Framework Types, 5th edition, Elsevier, London, England (2001), which is herein fully incorporated by reference.

Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., Introduction to Zeolite Science and Practice, Second Completely Revised and Expanded Edition, Volume 137, pages 1–67, Elsevier Science, B. V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. patent application Ser. No. 09/511,943 filed Feb. 24, 2000, now U.S. Pat. No. 6,743,747 (integrated hydrocarbon co-catalyst), PCT WO 01/64340 published Sep. 7, 2001 (thorium containing molecular sieve), and R. Szostak, Handbook of Molecular Sieves, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001, now U.S. Pat. No. 6,812,72 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

Molecular Sieve Synthesis

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a preferred embodiment the molecular sieves are synthesized by forming a reaction product of a source of silicon, a source of aluminum, a source of phosphorous, an organic templating agent, preferably a nitrogen containing organic templating agent, and one or more polymeric bases. This particularly preferred embodiment results in the synthesis of a silicoaluminophosphate crystalline material that is then isolated by filtration, centrifugation and/or decanting.

Non-limiting examples of silicon sources include a silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $ALPO_4$, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6) hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butylamine, ethylenediamine, pyrrolidine, and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminum-, and phosphorous-source, and a polymeric base.

Polymeric bases, especially polymeric bases that are soluble or non-ionic, useful in the invention, are those having a pH sufficient to control the pH desired for synthesizing a given molecular sieve, especially a SAPO molecular sieve. In a preferred embodiment, the polymeric base is soluble or the polymeric base is non-ionic, preferably the polymeric base is a non-ionic and soluble polymeric base, and most preferably the polymeric base is a polymeric imine. In one embodiment, the polymeric base of the invention has a pH in an aqueous solution, preferably water, from greater than 7 to about 14, more preferably from about 8 to about 14, most preferably from about 9 to 14.

In another embodiment, the non-volatile polymeric base is represented by the formula: (R—NH)$_x$, where (R—NH) is a polymeric or monomeric unit where R contains from 1 to 20 carbon atoms, preferably from 1 to 10 carbon atoms, more preferably from 1 to 6 carbon atoms, and most preferably from 1 to 4 carbon atoms; x is an integer from 1 to 500,000. In one embodiment, R is a linear, branched, or cyclic polymer, monomeric, chain, preferably a linear polymer chain having from 1 to 20 carbon atoms.

In another embodiment, the polymeric base is a water miscible polymeric base, preferably in an aqueous solution. In yet another embodiment, the polymeric base is a polyethylenimine that is represented by the following general formula:

(—NHCH$_2$CH$_2$—)$_m$[—N(CH$_2$CH$_2$NH$_2$)CH$_2$CH$_2$—]$_n$), wherein m is from 10 to 20,000, and n is from 0 to 2,000, preferably from 1 to 2000.

In another embodiment, the polymeric base of the invention has a average molecular weight from about 500 to about 1,000,000, preferably from about 2,000 to about 800,000, more preferably from about 10,000 to about 750,000, and most preferably from about 50,000 to about 750,000.

In another embodiment, the mole ratio of the monomeric unit of the polymeric base of the invention, containing one basic group, to the templating agent(s) is less than 20, preferably less than 12, more preferably less than 10, even more preferably less than 8, still even more preferably less than 5, and most preferably less than 4.

Non-limiting examples of polymer bases include: epichlorohydrin modified polyethylenimine, ethoxylated polyethylenimine, polypropylenimine diamine dendrimers (DAB-Am-n), poly(allylamine) [CH$_2$CH(CH$_2$NH$_2$)]$_n$, poly(1,2-dihydro-2,2,4-trimethylquinoline), and poly(dimethylamine-co-epichlorohydrin-co-ethylenediamine).

In another embodiment the invention is directed to a method for synthesizing a molecular sieve utilizing a templating agent, preferably an organic templating agent such as an organic amine, an ammonium salt and/or an ammonium hydroxide, in combination with a polymeric base such as polyethylenimine.

In a typical synthesis of the molecular sieve, the phosphorous-, aluminum-, and/or silicon-containing components are mixed, preferably while stirring and/or agitation and/or seeding with a crystalline material, optionally with an alkali metal, in a solvent such as water, and one or more templating agents and a polymeric base, to form a synthesis mixture that is then heated under crystallization conditions of pressure and temperature as described in U.S. Pat. Nos. 4,440,871, 4,861,743, 5,096,684, and 5,126,308, which are all herein fully incorporated by reference. The polymeric base is combined with the at least one templating agent, and one or more of the aluminum source, phosphorous source, and silicon source, in any order, for example, simultaneously with one or more of the sources, premixed with one or more of the sources and/or templating agent, after combining the sources and the templating agent, and the like.

Generally, the synthesis mixture described above is sealed in a vessel and heated, preferably under autogenous pressure, to a temperature in the range of from about 80° C. to about 250° C., preferably from about 100° C. to about 250° C., more preferably from about 125° C. to about 225° C., even more preferably from about 150° C. to about 180° C. In another embodiment, the hydrothermal crystallization temperature is less than 225° C., preferably less than 200° C. to about 80° C., and more preferably less than 195° C. to about 100° C.

In yet another embodiment, the crystallization temperature is increased gradually or stepwise during synthesis, preferably the crystallization temperature is maintained constant, for a period of time effective to form a crystalline product. The time required to form the crystalline product is typically from immediately up to several weeks, the duration of which is usually dependent on the temperature; the higher the temperature the shorter the duration. In one embodiment, the crystalline product is formed under heating from about 30 minutes to around 2 weeks, preferably from about 45 minutes to about 240 hours, and more preferably from about 1 hour to about 120 hours.

In one embodiment, the synthesis of a molecular sieve is aided by seeds from another or the same framework type molecular sieve.

The hydrothermal crystallization is carried out with or without agitation or stirring, for example stirring or tumbling. The stirring or agitation during the crystallization period may be continuous or intermittent, preferably continuous agitation. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

One method for crystallization involves subjecting an aqueous reaction mixture containing an excess amount of a templating agent and polymeric base, subjecting the mixture to crystallization under hydrothermal conditions, establishing an equilibrium between molecular sieve formation and dissolution, and then, removing some of the excess templating agent and/or organic base to inhibit dissolution of the molecular sieve. See for example U.S. Pat. No. 5,296,208, which is herein fully incorporated by reference.

Another method of crystallization is directed to not stirring a reaction mixture, for example a reaction mixture containing at a minimum, a silicon-, an aluminum-, and/or a phosphorous-composition, with a templating agent and a polymeric base, for a period of time during crystallization. See PCT WO 01/47810 published Jul. 5, 2001, which is herein fully incorporated by reference.

Other methods for synthesizing molecular sieves or modifying molecular sieves are described in U.S. Pat. No. 5,879,655 (controlling the ratio of the templating agent to phosphorous), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorous modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001, now U.S. Pat. No. 6,503,863 (cooling molecular sieve), U.S. patent application Ser. No. 09/615,526 filed Jul. 13, 2000, now U.S. Pat. No. 4,448,197 (metal impregnation including copper), U.S. patent application Ser. No. 09/672,469 filed Sep. 28, 2000, now U.S. Pat. No. 6,521,812 (conductive microfilter), and U.S. patent application Ser. No. 09/754,812 filed Jan. 4, 2001, now U.S. Pat. No. 6,537,941 (freeze drying the molecular sieve), which are all herein fully incorporated by reference.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

Molecular sieve have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10, and more preferably from about 0.32 to about 0.15.

The pH of a reaction mixture containing at a minimum a silicon-, aluminum-, and/or phosphorous-composition, a templating agent, and a polymeric base should be in the range of from 2 to 10, preferably in the range of from 4 to 9, and most preferably in the range of from 5 to 8. The pH can be controlled by the addition of basic or acidic compounds as necessary to maintain the pH during the synthesis in the preferred range of from 4 to 9. In another embodiment, the templating agent and/or polymeric base is added to the reaction mixture of the silicon source and phosphorous source such that the pH of the reaction mixture does not exceed 10.

In one embodiment, the molecular sieves of the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

Method for Making Molecular Sieve Catalyst Compositions

Once the molecular sieve is synthesized, depending on the requirements of the particular conversion process, the molecular sieve is then formulated into a molecular sieve catalyst composition, particularly for commercial use. The molecular sieves synthesized above are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by well-known techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 5, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve synthesized above, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In one embodiment, the binder, the molecular sieve and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, are in the same or different liquid, and are combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 μm to about 300 μm, preferably from about 50 μm to about 250 μm, more preferably from about 50 μm to about 200 μm, and most preferably from about 65 μm to about 90 μm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve in powder form.

Generally, the size of the powder is controlled to some extent by the solids content of the slurry. However, control of the size of the catalyst composition and its spherical characteristics are controllable by varying the slurry feed properties and conditions of atomization.

Other methods for forming a molecular sieve catalyst composition are described in U.S. patent application Ser. No. 09/617,714 filed Jul. 17, 2000, now U.S. Pat. No. 6,509,290 (spray drying using a recycled molecular sieve catalyst composition), which is herein incorporated by reference.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 2 hours.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition, in particular where the molecular sieve is a reaction product of the combination of a silicon-, phosphorous-, and aluminum-sources, a templating agent, and a polymeric base, more particularly a silicoaluminophosphate catalyst composition (SAPO) are described in, for example, U.S. Pat. No. 5,185,310 (heating molecular sieve of gel alumina and water to 450° C.), PCT WO 00/75072 published Dec. 14, 2000 (heating to leave an amount of template), and U.S. application Ser. No. 09/558,774 filed Apr. 26, 2000, now U.S. Pat. No. 6,498,120 (rejuvenation of molecular sieve), which are all herein fully incorporated by reference.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 5, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve synthesized above, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In one embodiment, the binder, the molecular sieve and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, are in the same or different liquid, and are combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 μm to about 300 μm, preferably from about 50 μm to about 250 μm, more preferably from about 50 μm to about 200 μm, and most preferably from about 65 μm to about 90 μm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve in powder form.

Generally, the size of the powder is controlled to some extent by the solids content of the slurry. However, control of the size of the catalyst composition and its spherical characteristics are controllable by varying the slurry feed properties and conditions of atomization.

Other methods for forming a molecular sieve catalyst composition are described in U.S. patent application Ser. No. 09/617,714 filed Jul. 17, 2000, now U.S. Pat. No. 6,509,290 (spray drying using a recycled molecular sieve catalyst composition), which is herein incorporated by reference.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 2 hours.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition, in particular where the molecular sieve is a reaction product of the combination of a silicon-, phosphorous-, and aluminum-sources, a templating agent, and a polymeric base, more particularly a silicoaluminophosphate catalyst composition (SAPO) are described in, for example, U.S. Pat. No. 5,185,310 (heating molecular sieve of gel alumina and water to 450° C.), PCT WO 00/75072 published Dec. 14, 2000 (heating to leave an amount of template), and U.S. application Ser. No. 09/558,774 filed Apr. 26, 2000, now U.S. Pat. No. 6,498,120 (rejuvenation of molecular sieve), which are all herein fully incorporated by reference.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are nser reactors generally described in Riser Reactor, Fluidization and Fluid-Particle Systems, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000, now embodied in U.S. Patent Publication No. 2005-015284 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor (s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar composition, or contain varying proportions of the same or different feedstock with the same or different diluent.

During the conversion of oxygenates to light olefins, carbonaceous deposits accumulate on the catalyst used to promote the conversion reaction. At some point, the build up of these carbonaceous deposits causes a reduction in the capability of the catalyst to convert the oxygenate feed to light olefins. At this point, the catalyst is partially deactivated. When a catalyst can no longer convert an oxygenate to an olefin product, the catalyst is considered to be fully deactivated. As a step in the process of the present invention, a portion of the catalyst is withdrawn from the reactor apparatus and at least a portion of the portion removed from the reactor is partially, if not fully, regenerated in a regenerator. By regeneration, it is meant that the carbonaceous deposits are at least partially removed from the catalyst. Desirably, the portion of the catalyst withdrawn from the reactor is at least partially deactivated. The remaining portion of the catalyst in the reactor apparatus is re-circulated without regeneration. The regenerated catalyst, with or without cooling, is then returned to the reactor. Desirably, the rate of withdrawing the portion of the catalyst for regeneration is from about 0.1% to about 99% of the rate of the catalyst exiting the reactor. More desirably, the rate is from about 0.2% to about 50%, and, most desirably, from about 0.5% to about 5%.

Desirably, the catalyst regeneration is carried out in the presence of a gas comprising oxygen. Air and air diluted with nitrogen or $CO_2$ are desired regeneration gases. The oxygen concentration in air can be reduced to a controlled level to minimize overheating of, or creating hot spots in, the regenerator. The catalyst may also be regenerated reductively with hydrogen, mixtures of hydrogen and carbon monoxide, or other suitable reducing gases.

The catalyst may be regenerated in any number of methods—batch, continuous, semi-continuous, or a combination thereof. Continuous catalyst regeneration is a desired method. Desirably, the catalyst is regenerated to a level of remaining coke from about 0.01 wt. % to about 15 wt. % of the weight of the catalyst.

The catalyst regeneration temperature should be from about 250° C. to about 750° C., and desirably from about 500° C. to about 700° C. A heat exchanger may be used to control the temperature within the regenerator to the desired range.

When the regenerated catalyst from the regenerator is returned to a reactor apparatus, it may be returned to the disengaging zone, the reaction zone, and/or the inlet zone. It may also be returned to a conduit which recirculates the catalyst from the disengaging zone to the inlet zone.

Desirably, catalyst regeneration is carried out on at least partially deactivated catalyst that has been stripped of most of readily removable organic materials (organics) in a stripper or stripping zone first. This stripping can be achieved by passing a stripping gas over the spent catalyst at an elevated temperature. Gases suitable for stripping include steam, nitrogen, helium, argon, methane, $CO_2$, CO, hydrogen, and mixtures thereof. A preferred gas is steam. Gas hourly space velocity (GHSV, based on volume of gas to volume of catalyst and coke) of the stripping gas is from about 0.1 $h^{-1}$ to about 20,000 $h^{-1}$. Acceptable temperatures of stripping are from about 250° C. to about 750° C., and desirably from about 350° C. to about 675° C.

The feedstock entering the reactor system is thus preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is the stripping zone under the conditions noted above.

The temperature useful to convert oxygenates to light olefins varies over a wide range depending, at least in part, on the catalyst, the fraction of regenerated catalyst in a catalyst mixture, and the configuration of the reactor apparatus and the reactor. The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C. Lower temperatures generally result in lower rates of reaction, and the formation rate of the desired light olefin products may become markedly slower. However, at temperatures greater than 700° C., the process may not form an optimum amount of light olefin products, and the rate at which coke and light saturates form on the catalyst may become too high.

Light olefins will form—although not necessarily in optimum amounts—at a wide range of pressures including, but not limited to, autogeneous pressures and pressures from about 0.1 kPa to about 100 MPa. A desired pressure is from about 6.9 kPa to about 34 MPa and most desirably from about 20 kPa to about 500 kPa. The foregoing pressures do not include that of a diluent, if any, and refer to the partial pressure of the feed as it relates to oxygenate compounds and/or mixtures thereof. Pressures outside of the stated ranges may be used and are not excluded from the scope of the invention. Lower and upper extremes of pressure may adversely affect selectivity, conversion, coking rate, and/or reaction rate; however, light olefins will still form and, for that reason, these extremes of pressure are considered part of the present invention.

A wide range of WHSV's for the oxygenate conversion reaction, defined as weight of total oxygenate to the reaction zone per hour per weight of molecular sieve in the catalyst in the reaction zone, function with the present invention. The total oxygenate to the reaction zone includes all oxygenate in both the vapor and liquid phase. Although the catalyst may contain other materials which act as inerts, fillers or binders, the WHSV is calculated using only the weight of molecular sieve in the catalyst in the reaction zone. The WHSV is desirably high enough to maintain the catalyst in a fluidized state under the reaction conditions and within the reactor configuration and design.

Generally, the WHSV is from about 1 $hr^{-1}$ to about 5000 $hr^{-1}$, desirably from about 2 $hr^{-1}$ to about 3000 $hr^{-1}$, and most desirably from about 5 $hr^{-1}$ to about 1500 $hr^{-1}$. For a feed comprising methanol, dimethyl ether, or mixtures thereof, the WHSV is desirably at least about 20 $hr^{-1}$ and more desirably from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, now U.S. Pat. No. 6,552,240, which is herein incorporated by reference.

A fluidized bed regenerator may be operated in dense, turbulent, or circulating fluid bed (riser) mode. A dense or turbulent mode of operation is characterized by a lower dense phase and an upper dilute phase, and is generally encountered when the superficial gas velocity of the fluidization gas is between 0.01–2 m/sec. The mixing of solids in the dense zone is very good, and thus results in a fairly uniform temperature within the dense phase, even though the oxidation of carbonaceous deposits in the regenerator is very exothermic. In the upper dilute phase, the interchange of solids is not so rapid, and any exothermic reactions occurring in the dilute phase will result in a temperature increase as the fluidization gas passes through this zone.

A fluidized bed regenerator may also operate in a circulating fluid bed or "riser" mode. Such a mode of operation is characterized by a dense phase of catalyst flowing with the regeneration gas in a "riser", followed by disengaging of solids from regeneration gases in a disengaging zone to form a dilute phase. In a "riser" mode, the dilute phase may be a quiescent zone outside the riser where catalyst separates by gravity, or it may occur in a cyclone that is close-coupled to the riser exit, where catalyst separates by centrifigal force.

Regardless of the mode, the dense phase is where the coke burning reaction is intended to occur, and the dilute phase forms in the zone(s) where catalyst separation from the gas begins.

Secondary reactions may occur in the dilute phase, resulting in temperature increases above the average temperature in the dense phase. These temperature differences are reduced by the addition of a CO oxidation metal.

The process of the present invention is continued for a period of time sufficient to produce the desired light olefins. A steady state or semi-steady state production of light olefins may be attained during this period of time, largely determined by the reaction temperature, the pressure, the catalyst selected, the amount of recirculated spent catalyst, the level of regeneration, the weight hourly space velocity, the superficial velocity, and other selected process design characteristics.

Oxygenate conversion should be maintained sufficiently high to avoid the need for commercially unacceptable levels of feed recycling. While 100% oxygenate conversion is desired for the purpose of completely avoiding feed recycle, a reduction in unwanted by-products is observed frequently when the conversion is about 98% or less. Since recycling up to as much as about 50% of the feed can be commercially acceptable, conversion rates from about 50% to about 98% are desired. Conversion rates may be maintained in this range—50% to about 98%—using a number of methods familiar to persons of ordinary skill in the art. Examples include, but are not necessarily limited to, adjusting one or more of the following: reaction temperature; pressure; flow rate (weight hourly space velocity and/or gas superficial velocity); catalyst recirculation rate; reactor apparatus configuration; reactor configuration; feed composition; amount of liquid feed relative to vapor feed; amount of recirculated catalyst; degree of catalyst regeneration; and other parameters which affect the conversion.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the processes for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is a Group IIIA or VIII element from the Periodic Table of Elements) molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. A heat exchanger may be used to control the temperature within the regenerator to the desired range. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

Metals useful in the present invention for promoting oxidation of carbon monoxide to carbon dioxide under catalyst regeneration conditions are described in U.S. Pat. Nos. 4,072,600 and 4,350,614 to Schwartz, the entire contents of each being incorporated herein by reference. Such metals are oxidation promoters selected from the group consisting of platinum, palladium, iridium, osmium, rhodium, ruthenium, rhenium, and combination thereof. The catalyst composition may comprise, for example, from about 0.01 ppm to about 100 ppm by weight oxidation promoter, usually from about 0.01 ppm to about 50 ppm by weight, preferably from about 0.01 ppm to about 5 ppm by weight.

Similarly, U.S. Pat. No. 4,151,112 to Gladrow et al., incorporated herein by reference, describes a hydrocarbon conversion catalyst for promoting the oxidation of carbon monoxide to carbon dioxide during regeneration of the catalyst by the burning of coke therefrom. Gladrow et al. disclose metals or compounds thereof which promotes the combustion of CO to $CO_2$ under conditions which are employed to regenerate the spent catalyst by burning the coke deposited thereon in the presence of oxygen. Accordingly, the catalyst will contain one or more metals (or compounds thereof) selected from Periods 5 and 6 of Group VIII of the Periodic Table (Handbook of Chemistry and Physics, 38th Ed., 1957), rhenium, chromium and manganese or their compounds. Specific examples of such metals include platinum, palladium, rhenium, iridium, ruthenium, rhodium, osmium, manganese, etc. The aforedescribed metals may also be present in the oxidized state of an oxide, sulfide, or other. Such metals or compounds are encompassed by the term "CO oxidation metal" used to describe the present invention and are thus suited to use in the present invention.

For purposes of the present invention, "CO oxidation metal," "CO combustion promoter" and "CO oxidation promoter are considered equivalent terms and encompass compounded metal and/or free metal.

The CO oxidation metal can be added to the catalyst used to effect conversion of oxygenates to olefins in several ways. In one aspect of the invention CO oxidation metal is added indirectly to the catalyst by introducing into the catalyst inventory at any suitable point of the process a separate particle containing CO oxidation metal which contacts the catalyst during the process, transferring at least a portion of the CO oxidation metal thereto.

Such a separate particle can comprise an inorganic porous oxide used as a and will include any of the readily available porous materials such as alumina, boria, silica, chromia, magnesia, zirconia, titania, the like, and mixtures thereof. These materials may also include one or more of the various well known clays such as montmorillonite, kaolin, halloysite, bentonite, attapulgite, and the like. Preferably, the inorganic porous oxide will be one or more of the conventional siliceous varieties containing a major amount of silica and a minor amount of an oxide of at least one metal in Groups II-A, III-A and IV-B of the Periodic Table (Handbook of Chemistry and Physics, 38th Ed., 1957). Representative materials include silica-alumina, silica-magnesia, silica-zirconia, silica-thoria, silica-titania, silica-alumina-zirconia, magnesia, etc. The most preferred inorganic porous oxide used as a support for the CO oxidation promoter is alumina. The most preferred inorganic porous oxide matrix material is silica-alumina. As is generally known, these materials are typically prepared from silica hydrogel or hydrosol, which is mixed with alumina to secure the desired silica-alumina composition. The alumina content will typically range from about 5 to 40 wt. % with the preferred composition having an alumina content of about 10 to 35 wt. %. Various procedures are described in the literature for making silica-alumina, e.g., U.S. Pat. Nos. 2,908,635 and 2,844,523.

Preferably, the CO oxidation metal is added to the catalyst particle itself. Even more preferably, the CO oxidation metal is added to the catalyst particle in such a way as to maximize CO oxidation metal deposition on the catalyst particle surface while minimizing CO oxidation metal deposition on interior pore surfaces. The latter can be achieved by utilizing a CO oxidation metal-containing compound having a diameter larger than the pore opening of the catalyst particle surface.

The CO oxidation metal is incorporated into the separate particle or catalyst particle by known techniques such as impregnation and vapor deposition. Preferably, the CO oxidation metal is introduced by impregnation of the particle with a solution of a compound of one or more of the aforementioned metals in an amount sufficient to provide the desired concentration. For example, an aqueous solution of palladium nitrate and/or chloroplatinic acid may be contacted with a porous inorganic oxide support, to produce a slurry which may thereafter be filtered, dried, calcined, and/or pre-reduced with hydrogen or other suitable reducing agents. Organic soluble compounds of the CO oxidation metal may also be used. For example platinum acetylacetonate, $Pt(AcAc)_2$ can be used for introducing CO oxidation metal. Such a compound is especially useful inasmuch as it is large enough to be excluded from many molecular sieve pores. The resulting supported CO oxidation promoter may be calcined in accordance with procedures known to those skilled in the art.

The CO oxidation metal is generally present in an amount no greater than 5% based on total catalyst weight, e.g., an amount no greater than 1% based on total catalyst weight, say, in an amount no greater than 5000 ppm based on total catalyst weight, an amount no greater than 500 ppm based on total catalyst weight, or even an amount no greater than 100 ppm based on total catalyst weight.

In an embodiment where the CO oxidation metal is a Group VB metal, e.g., vanadium, the catalyst contains at least 5000 wppm, e.g., 5000 to 100000 wppm, say, 10000 to 50000 wppm CO oxidation metal.

For an embodiment of the present invention wherein the CO oxidation metal is platinum, platinum is present in an amount ranging from 0.1 to 10000 ppm based on total catalyst weight, e.g., the CO oxidation metal is present in an amount ranging from 1 to 5000 ppm based on total catalyst weight.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000, now U.S. Pat. No. 6,613,950) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, now U.S. Pat. No. 6,441,262, which is herein fully incorporated by reference.

Other methods for operating a regeneration system are in disclosed U.S. Pat. No. 6,290,916 (controlling moisture), which is herein fully incorporated by reference.

Desirably, the rate of catalyst, comprising molecular sieve and any other materials such as binders, fillers, etc., plus non-reactive solids, recirculated to recontact the feed is from about 1 to about 100 times, more desirably from about 10 to about 80 times, and most desirably from about 10 to about 50 times the total feed rate of oxygenates to the reactor. Desirably, a portion of the catalyst, comprising molecular sieve and any other materials such as binders, fillers, etc., is removed from the reactor for regeneration and recirculation back to the reactor at a rate of from about 0.1 times to about 10 times, more desirably from about 0.2 to about 5 times, and most desirably from about 0.3 to about 3 times the total feed rate of oxygenates to the reactor. One skilled in the art will appreciate that the non-reactive solids may also be regenerated with the catalyst in the manner described above.

A preferred embodiment of a reactor system for the present invention is a circulating fluid bed reactor with continuous regeneration, similar to a modem fluid catalytic cracker. Fixed beds are not practical for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, preferably a gas comprising oxygen, most preferably air, to burn off coke from the catalyst, which restores the catalyst activity. The conditions of temperature, oxygen partial pressure, and residence time in the regenerator should be selected to achieve a coke content on regenerated catalyst of less than about 2 wt %, preferably less than about 0.5 wt %. At least a portion of the regenerated catalyst should be returned to the reactor.

It is important for the reactor to be designed such that a relatively high average level of coke is maintained in the reactor—an amount greater than about 1.5 wt %, preferably in the range of from about 2 wt % to about 30 wt %, most preferably in the range of from about 2 wt % to about 20 wt %. If the reactor is a high velocity fluidized bed reactor (sometimes referred to as a riser reactor), then a portion of the catalyst exiting the top of the reactor must be returned to the reactor inlet. This is different from a typical Fluid Catalytic Cracker (FCC) riser reactor, where all or most of the catalyst exiting the top of the reactor is sent to the regenerator. The return of coked catalyst directly to the reactor, without regenerating the coked catalyst, allows the average coke level in the reactor to build up to a preferred level. By adjusting the ratio of the flow of the coked catalyst between the regenerator and the reactor, a preferred level of coking, or "desirable carbonaceous deposits," can be maintained.

If the fluidized bed reactor is designed with low gas velocities, below about 2 m/sec, then cyclones may be used to return catalyst fines to the fluidized bed reaction zone. Such reactors generally have high recirculation rates of solids within the fluidized bed, which allows the coke level on the catalyst to build to a preferred level.

In order to determine the level of coke in the reactor and in the regenerator, small samples of catalyst periodically may be withdrawn from various points in the recirculating system for measurement of carbon content. The reaction parameters may be adjusted accordingly.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, the optimum level of coke on the molecular sieve catalyst composition in the reaction zone is maintained by controlling the flow of the regenerated molecular sieve catalyst composition or cooled regenerated molecular sieve catalyst composition from the regeneration system to the reactor system. There are many techniques for controlling the flow of a molecular sieve catalyst composition described in Michael Louge, Experimental Techniques, Circulating Fluidized Beds, Grace, Avidan and Knowlton, eds., Blackie, 1997 (336–337), which is herein incorporated by reference. This is referred to as the complete regeneration mode. In another embodiment, the optimum level of coke on the molecular sieve catalyst composition in the reaction zone is maintained by controlling the flow rate of the oxygen-containing gas flow to the regenerator. This is referred to as the partial regeneration mode.

Coke levels on the molecular sieve catalyst composition is measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one preferred embodiment, the molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated catalyst and catalyst that has ranging levels of carbonaceous deposits. The measured level of carbonaceous deposits thus represents an average of the levels an individual catalyst particle.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in Kirk-Othmer Encyclopedia of Chemical Technology, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000, now U.S. Pat. No. 6,593,506 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent gas withdrawn from the reactor or converting those products produced as a result of the recovery system utilized.

In one embodiment, the effluent gas withdrawn from the reactor is passed through a recovery system producing one or more hydrocarbon containing stream(s), in particular, a three or more carbon atom ($C_3^+$) hydrocarbon containing stream. In this embodiment, the $C_3^+$ hydrocarbon containing stream is passed through a first fractionation zone producing a crude $C_3$ hydrocarbon and a $C_4^+$ hydrocarbon containing stream, the $C_4^+$ hydrocarbon containing stream is passed through a second fractionation zone producing a crude $C_4$ hydrocarbon and a $C_5^+$ hydrocarbon containing stream. The four or more carbon hydrocarbons include butenes such as butene-1 and butene-2, butadienes, saturated butanes, and isobutanes.

The process of the present invention is desirably carried out in a reactor apparatus which comprises an inlet zone, a reaction zone, and a disengaging zone. When the process of the present invention is conducted in this type of reactor apparatus, at least a portion of the catalyst/solids is recirculated from the disengaging zone to the inlet zone to maintain the reactor at near isothermal conditions. At least a portion of the vapor feed then mixes with the catalyst/solids in the inlet zone and is directed to the reaction zone in which the oxygenate to olefin conversion reaction takes place. Optionally, a liquid feed and/or diluent portion of the total feed or various sub-portions thereof may be directed to the inlet zone and/or to one or more locations in the reaction zone. With this apparatus, the catalyst/solids can be recirculated either inside the reactor apparatus or external to the rector apparatus as the catalyst/solids are recirculated from the disengaging zone to the inlet zone and/or the reaction zone. As also described, an additional portion of the catalyst/solids can optionally be removed from the reactor apparatus and sent to a regenerator to regenerate the catalyst. Catalyst/solids from the regenerator can be returned to any of the three zones, or may be directed to a conduit which serves to recirculate the catalyst/solids from the disengaging zone to the inlet zone or reaction zone.

An embodiment of a reactor apparatus useful in the present invention is depicted generally as 300 in FIG. 1. An oxygenate feed 303 may be pretreated by at least partially vaporizing in a preheater. The methanol feed is mixed with catalyst from line 327 which includes unregenerated (coked) catalyst from line 324 regulated by valve 330 and/or regenerated catalyst from line 412 regulated by valve 415 at the bottom of the riser reactor 306, in inlet zone 304. An inert gas and/or steam 403 may be used to dilute the oxygenate, lift the catalyst streams, and keep pressure instrument lines clear of catalyst. This inert gas and/or steam mixes with the oxygenate and catalyst in the reactor 306 whose temperature can be monitored at various locations 309. The reaction is exothermic, and the preferred reaction temperature, in the range of from about 300° C. to about 500° C., is maintained by removing heat. Heat can be removed by any suitable means, including but not necessarily limited to cooling the reactor with a catalyst cooler 406, feeding some of the methanol as a liquid, cooling the catalyst feed to the reactor, or any combination of these methods.

The reactor effluent, containing products, coked catalyst, diluents, and unconverted feed, should flow to a disengaging zone 312. In the disengaging zone, coked catalyst is separated from the gaseous materials which are taken off via line 345 by means of gravity and/or cyclone separators with diplegs, 318 and 321. A portion of the coked catalyst is returned to the reactor inlet through line 324 controlled by valve 330. The portion of coked catalyst to be regenerated is first sent to a stripping zone 333, where steam or other inert gas is used to recover adsorbed hydrocarbons from the catalyst. Stripped spent coked catalyst should flow via line 339 controlled by valve 342 to the regenerator vessel 401. The portion of the catalyst sent to the regenerator vessel 401 should be contacted with a regeneration medium, preferably a gas comprising oxygen, e.g., air, introduced through the bottom regenerator inlet, at temperatures, pressures, and residence times that are capable of burning coke off of the catalyst and down to a level of less than about 0.5 wt %, as described above. The preferred temperature in the regenerator vessel is in the range of from about 550° C. to about 700° C., the preferred oxygen concentration in the gas leaving the regenerator is in the range of from about 0.1 vol % to about 5 vol %, and the preferred residence time is in the range of from about 1 to about 100 minutes.

The burning off of coke is exothermic. The temperature may be maintained at a suitable level by any acceptable method, including but not limited to feeding cooler gas, cooling the catalyst in the regenerator vessel with a cat cooler 406, or a combination of these methods.

The regenerated catalyst is sent to the reactor 306 via lines 409 and 412, controlled by valve 415, where it mixes with the recirculated coked catalyst from line 324 in line 327 and eventually with the oxygenate feed from line 303. The regenerated catalyst may be lifted to the reactor 306 by means of an inert gas, steam, or methanol vapor introduced via lift gas line 403. The process should repeat itself in a continuous or semi-continuous manner. The hot reactor product gases should be cooled, the water byproduct condensed and collected, and the desired olefin product gases recovered for further processing.

In order to determine the level of coke in the reactor and in the regenerator, small samples of catalyst periodically may be withdrawn from various points in the recirculating system for measurement of carbon content. The reaction parameters may be adjusted accordingly.

General Experimental Procedure

MTO Reaction Tests and GC Analysis

Methanol-to-Olefins (MTO) conversion reactions were carried out in a tubular micro flow-reactor at 2.5 WHSV, 450° C. and 276 KPa (40 psia), unless specified otherwise. The reactor, 0.25" in outer diameter, 8" in length and 0.04" in thickness, was made of silicosteel.

The effluent from the tubular reactor was collected in a Valco sampling valve with 15 250 □l sample loops. The collected effluent samples were analyzed by on-line gas chromatography (Hewlett Packard 6890) equipped with a flame ionization detector. The chromatographic column used was a 150 meter, 0.25 mm (inner diameter) fused silica capillary column (Model No. Petrocol DH 150).

The gas phase products were also collected in a stainless steel bomb after the effluent flowed pass the aforementioned sampling valve and a knockout trap for removing liquids, such as water and methanol.

The selectivity (wt %) data reported in the tables were conversion-weighed averages, and were calculated based on the products that exited the reactor. In other words, water and coke were not included as products in these calculations. $C_1$, $C_2^=$, $C_2^o$, $C_3^=$, $C_3^o$ and $C_4^=$ listed in the tables referred to methane, ethylene, ethane, propene, propane and butenes, respectively.

Temperature Programmed-Oxidation (TPO)

TPO (temperature programmed-oxidation) was used to measure the amount of carbon during coke-removing experiments. TPO was carried out by loading 5 to 10 mg of a MTO catalyst (5.2 wt % carbon, 37.9 wt % SAPO-34 and 56.9 wt % clay binder) in a quartz reactor. A carrier gas containing 1% $O_2$ in helium was introduced to the quartz reactor at a rate of 63 ml/minute. The reactor was heated at a constant rate of 13° C. per minute. The gas exiting the quartz reactor was directed to a methanator, which contained a ruthenium catalyst. This catalyst was operated at 400° C. to convert CO and $CO_2$ to methane. The methane produced was continuously measured with a flame ionization detector (FID). To measure the CO production during the TPO experiments, a $CO_2$ trap filled with ascarite (sodium hydroxide impregnated solids) was used to completely remove $CO_2$ from the exit gas before it was sent to the methanator. Therefore, the TPO signal (FID) acquired with the ascarite trap exclusively measured the amount of CO that was produced from the oxidation of carbon on the catalyst. Details of this technique are found in S. C. Fung and C. A. Querini, J. Cat., 138, 240 (1992) and C. A. Querini and S. C. Fung, J. Cat., 141, 389 (1993), incorporated herein by reference.

Wet Impregnation of Platinum Onto SAPO-34

Wet impregnation was used for loading Pt onto/into SAPO-34 catalyst. In a typical preparation for a catalyst loaded with 5000 wppm (parts per million by weight) Pt, 0.013 g of Pt(acetylacetonate)$_2$—or Pt(AcAc)$_2$—(99.9%, Aldrich) was dissolved in 2.2 ml of toluene. The amount of toluene used was enough to fill the mesoporous and macroporous volume of the catalyst. The solution was added dropwise to 1.0028 g of a de-templated SAPO-34. The wet mixture was dried in a vacuum oven for 1 hr to remove toluene. The resulting solid catalyst was then calcined at 350° C. for 2 hr in a furnace. The platinum concentration in such-prepared catalysts was confirmed by elemental analyses. Two SAPO-34 catalysts containing 2000 wppm Pt and 5000 wppm Pt, respectively, were prepared following the procedure. The impact of Pt on MTO selectivity and the effectiveness of these Pt-impregnated SAPO-34 catalyst in promoting the oxidation of CO were shown in Examples 3 to 5.

Pt reduction was carried out at 510° C. by flowing a stream of H$_2$ diluted with He (10 ml/min H$_2$ and 40 ml/min He) for 2 hr in a flow reactor. Oxidation was conducted in a stream of O$_2$ (50 ml/min) at 600° C. for 2 hr.

Hydrogen Chemisorption

Hydrogen chemisorption is used to determine the dispersion, or conversely, extent of agglomeration, of the Pt particles in the FCC CO promoter catalyst and the Pt-impregnated SAPO-34 catalyst. Hydrogen chemisorption measures how many hydrogen atoms are adsorbed by the total number of Pt atoms present on a catalyst. When the H/Pt atom ratio is 1, all Pt atoms in the catalyst are accessible by the hydrogen atom, i.e., the Pt particle is very small in the order of less than 10 Å. The supported Pt particles are said to be highly dispersed when the H/Pt is >0.7 and is moderately dispersed when H/Pt is 0.1 to 0.7. The dispersion of the supported Pt particles is low when H/Pt <0.1. Details of the analytical technique may be found in Structure of Metallic Catalyst, J. R. Anderson, Ch. 6, p. 295, Academic Press (1975).

EXAMPLE 1

A commercially available FCC CO promoter catalyst, containing 780 wppm Pt/Al$_2$O$_3$ (780 wppm Pt on alumina) was added to a MTO catalyst, which contained 7.2 wt % carbon, 37.1 wt % SAPO-34 and 55.7 wt % clay binder. The particle size of the MTO catalyst was about 100 micron. Four catalysts, containing 7.8 wppm, 39.0 wppm, 156 wppm, and 312 wppm Pt, respectively, were prepared by adding appropriate amount of the FCC CO promoter (Intercat, COP-850) to the MTO catalyst. Table 1 shows the effect of addition of the CO promoter on selectivity (wt %) for the MTO catalyst.

TABLE 1

| Pt wppm | C$_1$ Wt % | C$_2^-$ Wt % | C$_2$° wt % | C$_3^-$ Wt % | C$_3$° Wt % | C$_4^-$ Wt % | C$_2^-$ + C$_3^-$ wt % |
|---|---|---|---|---|---|---|---|
| 0 | 1.7 | 35.2 | 1.0 | 43.2 | 2.0 | 13.0 | 78.4 |
| 7.8 | 2.0 | 35.5 | 1.2 | 42.7 | 2.0 | 12.7 | 78.2 |
| 39 | 3.4 | 32.8 | 4.7 | 40.2 | 2.8 | 12.4 | 73.0 |
| 156 | 9.0 | 11.1 | 26.5 | 28.6 | 10.8 | 10.9 | 39.7 |
| 312 | 13.5 | 1.9 | 35.0 | 18.2 | 18.9 | 9.7 | 20.1 |

Data in Table 1 show that there was minimal effect on the prime olefins selectivity at low Pt concentrations. For example, at 7.8 wppm of Pt loading, the selectivity for C$_3^-$ only decreased by 0.5 wt % while selectivity for ethylene increased by 0.3 wt %.

When the concentration of Pt was increased by increasing the amount of the FCC CO promoter in the mixture, the data in table 1 show a clear detrimental effect on ethylene and propene selectivity, e.g., a decrease of 5.4 wt % at 39 wppm Pt.

Therefore, the amount of the FCC CO promoter added to the MTO reactor needs to be precisely controlled at a level that does not induce noticeable detrimental impact on the ethylene and propene selectivity.

EXAMPLE 2

A MTO catalyst containing 5.2 wt % carbon, 37.9 wt % SAPO-34 and 56.9 wt % clay binder was used in the TPO studies to investigate the effectiveness of the FCC CO promoter in the oxidation of CO to CO$_2$. An appropriate amount of the FCC CO promoter (Intercat COP-850) was added to the MTO catalyst so that the Pt concentration in the final mixture was 18.8 wppm. TPO experiments were performed both with and without the use of the ascarite trap so that both CO and CO$_2$ were measured. Table 2 shows carbon wt % evolved as CO and CO$_2$ for the MTO catalyst with or without the FCC CO promoter.

TABLE 2

| Pt wppm | Carbon wt % evolved as CO | Carbon wt % evolved as CO$_2$ | Total Carbon wt % |
|---|---|---|---|
| 0 | 3.3 | 1.9 | 5.2 |
| 18.8 | 0.2 | 5.0 | 5.2 |

The TPO data show that the presence of 18.8 wppm Pt greatly decreases the CO signal. The total amount of CO produced was equivalent to 0.2 wt. % carbon, a reduction of 94%. This suggests the presence of Pt promotes the oxidation of CO to CO$_2$.

EXAMPLE 3

Two platinum-containing catalysts were prepared by wet impregnation following the procedure detailed in the GENERAL EXPERIMENTAL PROCEDURE above. The Pt concentration of these two catalysts was 2000 wppm and 5000 wppm, respectively. Table 3 compares the selectivity data of the catalyst containing 5000 wppm Pt with that of the parent SAPO-34 with no Pt loading for the methanol to olefins reactions. The MTO reactions were performed at 450° C., 276 KPa (40 psia) and 25 WHSV.

TABLE 3

| Pt wppm | C$_1$ Wt % | C$_2^-$ Wt % | C$_2$° wt % | C$_3^-$ Wt % | C$_3$° Wt % | C$_4^-$ Wt % | C$_2^-$ + C$_3^-$ wt % |
|---|---|---|---|---|---|---|---|
| 0 | 1.0 | 28.2 | 1.2 | 38.6 | 7.1 | 17.5 | 66.8 |
| 5000 | 1.1 | 28.0 | 2.4 | 39.0 | 7.0 | 16.9 | 67.0 |

Note that the wet impregnation of 5000 wppm Pt onto SAPO-34 showed no impact on the performance of the SAPO-34 catalyst. For comparison, when Pt was introduced in the form of the FCC CO promoter a Pt concentration of 39 wppm showed significant impact on ethylene and propene selectivity (Example 1, Table 1).

Since the size of the platinum acetylacetonate is considerably larger than the pore opening of the SAPO-34 molecular sieve, the Pt acetylacetonate was mostly on the external surface of the SAPO-34 crystallites. Pt was not highly dispersed because the external surface of the SAPO-34 crystallites was only a small fraction of its total area, with most of its surface area being the surface area of the pores inside the crystals. Hydrogen chemisorption can be used to determine Pt dispersion as shown in Example 4.

EXAMPLE 4

Hydrogen chemisorption determined the dispersion of the Pt particles in the FCC CO promoter catalyst and the Pt-impregnated SAPO-34 catalyst. Hydrogen chemisorption measured how many hydrogen atoms are adsorbed by the total number of Pt atoms present on a catalyst. When the H/Pt atom ratio is 1, all Pt atoms in the catalyst are accessible by the hydrogen atom, i.e., the Pt particle is very small in the order of less than 10 Å. Table 4 shows that the H/Pt ratio of the FCC CO promoter catalyst is 0.90 indicating 90% of Pt atoms are surface atoms (small Pt particle size) and the Pt-impregnated SAPO-34 show a low H/Pt of 0.01 indicating large Pt particles size, and only 1% of the Pt atoms are surface atoms.

TABLE 4

| Pt catalyst | Pt (wppm) | H/Pt |
|---|---|---|
| FCC CO promoter | 780 | 0.9 |
| Pt-impregnated SAPO-34 | 2000 | 0.01 |

EXAMPLE 5

The Pt impregnated catalysts were reduced and oxidized prior to the MTO test reactions in lab flow reactor to simulate the reducing environment in the reactor zone and the oxidizing environment in the regenerator, respectively. Table 5 shows the selectivity data for a SAPO-34 catalyst impregnated with 2000 wppm of Pt.

TABLE 5

| Pt wppm | Treatment | $C_1$ Wt % | $C_2^=$ Wt % | $C_2^°$ wt % | $C_3^=$ Wt % | $C_3^°$ Wt % | $C_4^=$ Wt % | $C_2^= + C_3^=$ wt % |
|---|---|---|---|---|---|---|---|---|
| 0 | none | 0.8 | 33.1 | 0.8 | 42.5 | 2.9 | 15.3 | 75.6 |
| 2000 | none | 0.8 | 32.2 | 0.8 | 43.3 | 3.2 | 15.4 | 75.5 |
| 2000 | reduced | 1.2 | 32.7 | 1.7 | 42.9 | 4.0 | 14.1 | 75.6 |
| 2000 | oxidized | 1.0 | 33.7 | 1.1 | 42.6 | 4.0 | 14.0 | 76.3 |

Though $C_1$ to $C_3^°$ alkane selectivities appeared to increase moderately, there was no loss of ethylene and propylene selectivities following a simulated reaction/regeneration cycle.

EXAMPLE 6

The effectiveness of Pt-impregnated SAPO-34 catalysts in promoting the oxidation of CO to $CO_2$ was studied by the use of TPO. Pt- and carbon-containing samples for TPO studies were prepared by mixing the appropriate amount of a coke-containing MTO catalyst and the Pt-impregnated SAPO-34s. Two samples with Pt concentrations of 48 wppm and 121 wppm were thus prepared from the 2000 wppm and 5000 wppm Pt-impregnated SAPO-34s, respectively. The carbon content of both samples was 5.2 wt %. Table 6 shows the TPO data for these two samples along with that of a sample with no Pt.

TABLE 6

| Pt wppm | Carbon wt % evolved as CO | Carbon wt % evolved as $CO_2$ | Total Carbon wt % |
|---|---|---|---|
| 0 | 3.3 | 1.9 | 5.2 |
| 48 | 0.2 | 5.0 | 5.2 |
| 121 | 0.2 | 5.0 | 5.2 |

Although the Pt dispersion of these Pt-impregnated SAPO-34 catalysts were low they were very effective in converting CO into $CO_2$ at Pt concentrations comparable to that of the highly dispersed FCC CO promoter catalyst.

Thus, it appears that when the carbon monoxide oxidation metal-associated catalyst is moderately dispersed or at a low dispersion (e.g., when the carbon monoxide oxidation catalyst is added by wet impregnation of platinum acetylacetonate), it is as effective as a commercial FCC CO promoter in the conversion of CO to $CO_2$ in the regenerator of an oxygenate to olefin process and it shows no impact on the performance of the SAPO-34 catalyst, i.e., no loss in ethylene and propylene selectivity.

EXAMPLE 7

A fluidized bed reactor apparatus similar to that described as FIG. 1 is employed in an oxygenate conversion reaction process of the present invention. Thus some catalyst flows from catalyst stripper 333 to the regenerator vessel 401 and is returned from there to inlet zone 304, while some flows through line 324 and is returned to inlet zone 304 without regeneration. This apparatus was used to study the response in the reactor and regenerator to the addition of the same commercially available FCC CO combustion promoter catalyst discussed in Example 1 to an MTO catalyst.

Figure 2:
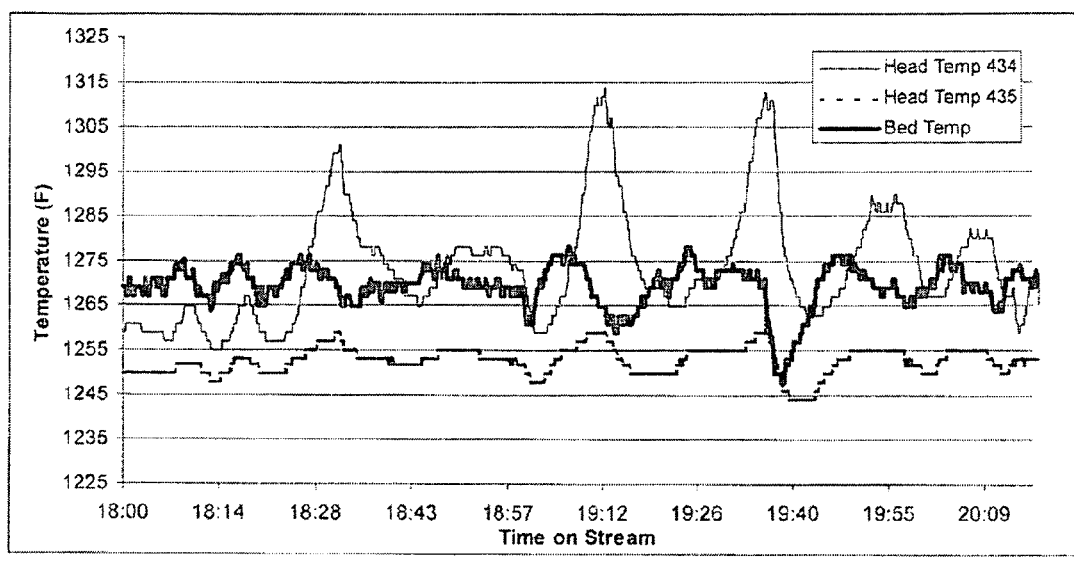
FIG. 2 depicts a profile of temperature over time measured at the regenerator head and regenerator bed of an oxygenate to olefin reactor apparatus, in the absence of CO oxidation metal-containing catalyst.
Figure 3:
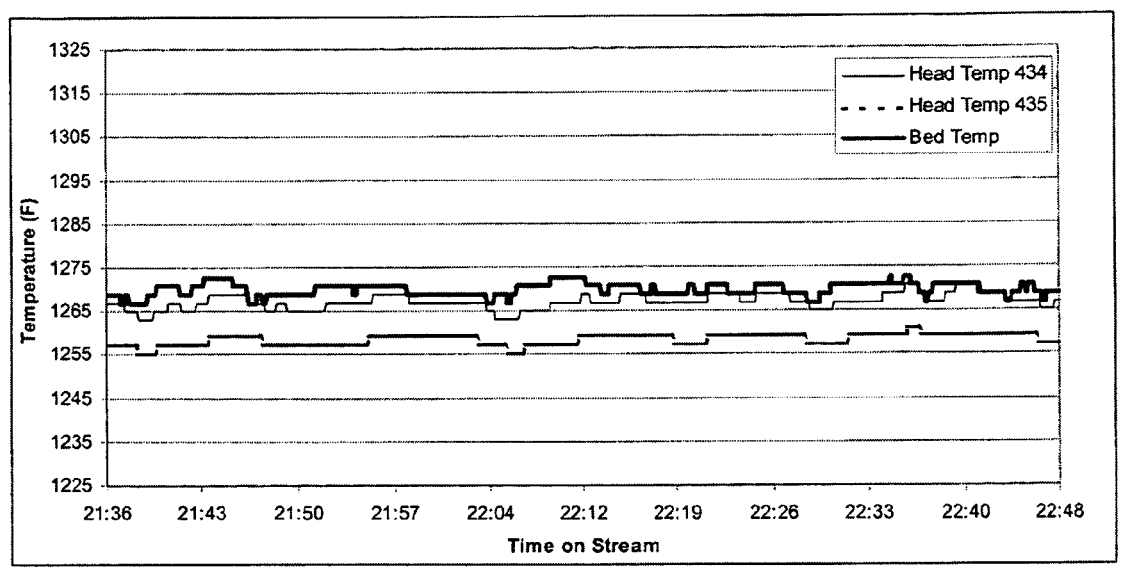
FIG. 3 depicts a profile of temperature over time for reactor measured at the regenerator head and regenerator bed of an oxygenate to olefin reactor, in the presence of CO oxidation metal-containing catalyst.

Prior to adding the CO combustion promoter, the upper, dilute disengaging zone of the regenerator often ran at a greater temperature than the regenerator bed temperature. Periodically, the head of the regenerator would undergo rapid, sometimes localized, temperature increases. FIG. 2 shows a regenerator head thermocouple undergoing rapid increases in temperature during routine, otherwise stable conditions. The data shown in FIG. 2 were obtained with a catalyst coke loading of 0.8 wt % in the regenerator. After these data were obtained, the FCC CO combustion promoter catalyst was physically mixed with the MTO catalyst at a concentration of 830 wppm promoter. As the promoter catalyst was 780 wppm Pt on $Al_2O_3$, the total concentration of Pt in the circulating catalyst was 0.65 wppm. FIG. 3 demonstrates that the addition of the promoter catalyst eliminated the periodic high temperature excursions. These data were also obtained with a catalyst coke loading of 0.8 wt % in the regenerator.

The addition of the promoter did not adversely affect the conversion of oxygenates to light olefins. In the apparatus shown in FIG. 1, methanol was fed at 25 psig with an average riser temperature of 450° C., a space velocity of 24–25 $hr^{-1}$, and a reactor catalyst coke loading of 7.0 wt %. In the two examples, first 0 and then 0.65 wppm Pt was added to the circulating catalyst. The products from the reaction were as listed in Table 7. Qualitative analyses of CO, $CO_2$, and $H_2$ indicated that these species were not affected either by 0.65 wppm of Pt in the circulating catalyst.

TABLE 7

|  |  | Case 1 | Case 2 |
|---|---|---|---|
| Pt Conc. | ppmw | 0 | 0.65 |
| Pressure | psig | 25 | 25 |
| Rxr Temp | C. | 450 | 450 |
| Rgn Temp | C. | 677 | 677 |
| Rxr Coke | wt % | 7.0 | 7.0 |
| Sp Velocity | hr-1 | 24.7 | 24.1 |
| Conversion | wt % | 91.7 | 90.1 |
| $C_1$ | wt % | 0.826 | 0.841 |
| $C_2^-$ | wt % | 33.7 | 33.4 |
| $C_2^o$ | wt % | 0.596 | 0.578 |
| $C_3^-$ | wt % | 42.5 | 42.3 |
| $C_3^o$ | wt % | 1.99 | 1.90 |
| $C_4^s$ | wt % | 12.7 | 13.0 |
| $C_5+$ | wt % | 4.41 | 4.38 |
| Coke | wt % | 3.29 | 3.53 |

The advantages of using the Pt catalyst as CO promoter in the MTO regenerator is that it provides effective conversion of CO to $CO_2$ in the MTO regenerator and at the same time does not adversely affect the ethylene and propylene selectivities when used in the MTO reactor.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

The invention claimed is:

1. A process for making an olefin product from an oxygenate feedstock comprising:
    a) contacting the feedstock in a reaction zone with a catalyst comprising i) a molecular sieve having defined pore openings and ii) a CO oxidation metal, under conditions effective to convert the feedstock into an olefin product stream comprising $C_2$–$C_3$ olefins and to form carbonaceous deposits on the catalyst so as to provide a carbon-containing catalyst;
    b) contacting at least a portion of the carbon-containing catalyst with a regeneration medium comprising oxygen in a regeneration zone comprising a fluid bed regenerator having a dense fluid phase and a dilute fluid phase under conditions effective to obtain a regenerated catalyst portion, wherein the difference between the temperature of said dilute phase and the temperature of said dense phase is no greater than 100° C.;
    c) introducing said regenerated catalyst portion into said reaction zone; and
    d) repeating steps a)–c);
wherein said olefin product stream from the reaction zone comprises at least 50% by weight of olefins based on the total amount of hydrocarbons produced; and wherein the selectivity of the process for ethylene and propylene differs by no more than ±5% to that of said process carried out in the absence of said CO oxidation metal.

2. The process of claim 1, wherein said difference is no greater than 50° C.

3. The process of claim 1, wherein said difference is no greater than 20° C.

4. The process of claim 1, wherein said difference is no greater than 10° C.

5. The process of claim 1, wherein the regenerated catalyst portion has less than 5.0 wt. % carbonaceous deposits.

6. The process of claim 1, wherein the regenerated catalyst portion has less than 3 wt. % carbonaceous deposits.

7. The process of claim 1, wherein the regenerated catalyst portion has less than 1 wt. % carbonaceous deposits.

8. The process of claim 1, wherein said carbon-containing catalyst has no less than 5 wt. % carbonaceous deposits.

9. The process of claim 1, wherein said carbon-containing catalyst has no less than 3 wt. % carbonaceous deposits.

10. The process of claim 1, wherein said carbon-containing catalyst has no less than 1 wt. % carbonaceous deposits.

11. The process of claim 1 wherein said CO oxidation metal comprises an element selected from the group consisting of Group VB, Group VIB, Group VIIB, and Group VIII metals.

12. The process of claim 11 wherein said Group VB metal is V, said Group VIB metal is selected from the group consisting of Cr, Mo and W, said Group VIIB metal is Mn, and said Group VIII metal is selected from the group consisting of Ni, Ru, Rh, Pd, Os, Ir, and Pt.

13. The process of claim 1 wherein said CO oxidation metal comprises Pt.

14. The process of claim 1 wherein said CO oxidation metal is added in a form having an external dimension greater than the diameter of said pore openings of the molecular sieve.

15. The process of claim 1 wherein said CO oxidation metal is added in the form of platinum acetylacetonate.

16. The process of claim 1 wherein said molecular sieve catalyst has a pore diameter of less than 5.0 Angstroms.

17. The process of claim 16 wherein the molecular sieve catalyst has at least one molecular sieve framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, and THO.

18. The process of claim 16 wherein the molecular sieve catalyst has at least one molecular sieve selected from the group consisting of erionite and chabazite, SAPO-34, SAPO-17, SAPO-18, and substituted groups thereof.

19. The process of claim 1, wherein the molecular sieve catalyst has a pore diameter of 5–10 Angstroms.

20. The process of claim 19, wherein the molecular sieve catalyst has at least one molecular sieve framework-type selected from the group consisting of MFI, MEL, MTW, EUO, MTT, HEU, FER, AFO, AEL, TON, and substituted groups thereof.

21. The process of claim 1 wherein there is no reduction in % selectivity to ethylene and propylene compared to said process carried out in the absence of said CO oxidation metal.

22. The process of claim 1 wherein said CO oxidation metal is present in an amount no greater than 5% based on total catalyst weight.

23. The process of claim 1 wherein said CO oxidation metal is present in an amount no greater than 1% based on total catalyst weight.

24. The process of claim 1 wherein said CO oxidation metal is present in an amount no greater than 5000 ppm based on total catalyst weight.

25. The process of claim 1 wherein said CO oxidation metal is present in an amount no greater than 500 ppm based on total catalyst weight.

26. The process of claim 1 wherein said CO oxidation metal is present in an amount no greater than 100 ppm based on total catalyst weight.

27. The process of claim 1 wherein said CO oxidation metal is platinum and is present in an amount ranging from 5 to 10000 ppm based on total catalyst weight.

28. The process of claim 1 wherein said CO oxidation metal is platinum and is present in an amount ranging from 100 to 5000 ppm based on total catalyst weight.

29. The process of claim 1 wherein said CO oxidation metal is vanadium and is present in an amount ranging from 10000 to 50000 ppm based on total catalyst weight.

30. The process of claim 1 wherein said CO oxidation metal is added to said process separately from said molecular sieve.

31. The process of claim 1 wherein said CO oxidation metal is added to said process through said regeneration zone.

32. The process of claim 1 wherein said CO oxidation metal is added to said process through said reaction zone.

33. The process of claim 1 wherein said CO oxidation metal is added to said catalyst by ion exchange.

34. The process of claim 1 wherein a temperature of 500° to 750° C. is maintained within said dense fluid phase of the regenerator.

35. The process of claim 13, where the dispersion level of said CO oxidation metal added to the system is between 0.01 to 0.7 H:Pt.

36. The process of claim 19, wherein the molecular sieve catalyst comprises a ZSM-4 or ZSM-5 molecular sieve catalyst.

* * * * *